US010280409B2

United States Patent
Goel et al.

(10) Patent No.: US 10,280,409 B2
(45) Date of Patent: May 7, 2019

(54) CODON OPTIMIZED POLYNUCLEOTIDE FOR HIGH LEVEL EXPRESSION OF CRM197

(71) Applicant: BIOLOGICAL E LIMITED, Hyderabad, Telangana (IN)

(72) Inventors: Akshay Goel, Hyderabad (IN); Ravi Pratap Narayan Mishra, Hyderabad (IN); Narender Dev Mantena, Hyderabad (IN); Mahima Datla, Hyderabad (IN)

(73) Assignee: BIOLOGICAL E LIMITED (IN)

( * ) Notice: Subject to any disclaimer, the term of this patent is extended or adjusted under 35 U.S.C. 154(b) by 0 days.

(21) Appl. No.: 15/523,616

(22) PCT Filed: Nov. 17, 2015

(86) PCT No.: PCT/IN2015/000427
§ 371 (c)(1),
(2) Date: May 1, 2017

(87) PCT Pub. No.: WO2016/079755
PCT Pub. Date: May 26, 2016

(65) Prior Publication Data
US 2017/0306302 A1   Oct. 26, 2017

(30) Foreign Application Priority Data

Nov. 20, 2014 (IN) ............................ 4045/CHE/2014

(51) Int. Cl.
| | |
|---|---|
| *C12N 9/10* | (2006.01) |
| *C07K 14/34* | (2006.01) |
| *C12N 15/10* | (2006.01) |
| *C12N 15/70* | (2006.01) |
| *C12N 15/74* | (2006.01) |
| *C12P 21/00* | (2006.01) |
| *C12P 21/02* | (2006.01) |
| *C07K 14/195* | (2006.01) |
| *G01N 33/573* | (2006.01) |

(52) U.S. Cl.
CPC .......... *C12N 9/1051* (2013.01); *C07K 14/195* (2013.01); *C07K 14/34* (2013.01); *C12N 9/1077* (2013.01); *C12N 15/10* (2013.01); *C12N 15/70* (2013.01); *C12N 15/74* (2013.01); *C12P 21/02* (2013.01); *G01N 33/573* (2013.01); *C07K 2319/00* (2013.01); *C12P 21/00* (2013.01)

(58) Field of Classification Search
None
See application file for complete search history.

(56) References Cited

U.S. PATENT DOCUMENTS

| | | | |
|---|---|---|---|
| 4,695,455 | A | 9/1987 | Barnes et al. |
| 4,755,465 | A | 7/1988 | Gray et al. |
| 4,861,595 | A | 8/1989 | Barnes et al. |
| 5,055,294 | A | 10/1991 | Gilroy |
| 5,128,130 | A | 7/1992 | Gilroy et al. |
| 5,169,760 | A | 12/1992 | Wilcox |
| 5,281,532 | A | 1/1994 | Rammler et al. |
| 5,614,382 | A | 3/1997 | Metcalf |
| 8,530,171 | B2 | 9/2013 | Retallack et al. |
| 2006/0270600 | A1 | 11/2006 | Mekada et al. |
| 2012/0128727 | A1 | 5/2012 | Baglioni et al. |
| 2012/0289688 | A1 | 11/2012 | Blais et al. |
| 2014/0050758 | A1 | 2/2014 | Dohottay et al. |

FOREIGN PATENT DOCUMENTS

| | | | |
|---|---|---|---|
| CN | 103266125 | 8/2013 | |
| WO | WO2011/042516 | 4/2011 | |
| WO | WO-2012140171 A1 * | 10/2012 | ........... C07K 14/195 |
| WO | WO2013/178974 | 12/2013 | |
| WO | WO2015/134402 | 9/2015 | |

OTHER PUBLICATIONS

Bishai et al., "High-level expression of a proteolytically sensitive diphtheria toxin fragment in *Escherichia coli*," J. Baeteriol. 169(11):5140-51 (Nov. 1987).
Greenfield et al., "Nucleotide sequence of the structural gene for diphtheria toxin carried by corynebacteriophage beta," Proc. Natl. Acad. Sci. USA 80(22):6853-7 (Nov. 1983).
International Search Report and Written Opinion dated Apr. 20, 2016 for International Application No. PCT/IN2015/000427.
Moskang et al., "Translocation of diphtheria toxin A-fragment to the cytosol. Role of the site of intergragment clevage," J. Biol. Chem. 264:15709-13 (Sep. 15, 1989).
Stefan et al., "Overexpression and purification of the recombinant diphtheria toxin variant CRM197 in *Escherichia coli*," J Biotechnol 156(4):245-52 (Dec. 20, 2011).
Uchida, et al., "Mutation in the Structural Gene for Diphtheria Toxin carried by Temperate Phage β," Nature New Biology, 233:8-11, (Sep. 1, 1971).

* cited by examiner

*Primary Examiner* — Brian Gangle
(74) *Attorney, Agent, or Firm* — Perkins Coie LLP

(57) ABSTRACT

The present invention relates to high level expression of bacterial toxoid or toxin protein of pharmacological interest by means of an optimized novel polynucleotide sequence and host transformed with the said polynucleotide. Specifically, the invention provides a method for high production of polypeptide $CRM_{197}$ wherein, the polynucleotide of the invention is used to transform a suitable host resulting in over-expression of corresponding proteins and a method for isolating the expressed polypeptide. More particularly, the present invention relates to high level expression of $CRM_{197}$ in *Escherichia coli* and a method for the isolation and purification thereof.

14 Claims, 9 Drawing Sheets

Specification includes a Sequence Listing.

1. Urea Solubilized pellet
2. Supernatant
3. Pellet Wash-1
4. Pellet Wash-2

SEQUENCE LISTING

```
<160> NUMBER OF SEQ ID NOS: 14

<210> SEQ ID NO 1
<211> LENGTH: 535
<212> TYPE: PRT
<213> ORGANISM: Artificial Sequence
<220> FEATURE:
<223> OTHER INFORMATION: Recombinant

<400> SEQUENCE: 1

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
```

```
            180                 185                 190
Arg Ser Val Gly Ser Ser Leu Ser Cys Ile Asn Leu Asp Trp Asp Val
            195                 200                 205

Ile Arg Asp Lys Thr Lys Thr Lys Ile Glu Ser Leu Lys Glu His Gly
210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
            245                 250                 255

His Pro Glu Leu Ser Glu Leu Lys Thr Val Thr Gly Thr Asn Pro Val
        260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
        290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
            325                 330                 335

Ser Leu Met Val Ala Gln Ala Ile Pro Leu Val Gly Glu Leu Val Asp
        340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
        370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
            405                 410                 415

Asp Ile Lys Ile Thr Ala Glu Asn Thr Pro Leu Pro Ile Ala Gly Val
        420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
        450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
            485                 490                 495

Glu Lys Ile His Ser Asn Glu Ile Ser Ser Asp Ser Ile Gly Val Leu
        500                 505                 510

Gly Tyr Gln Lys Thr Val Asp His Thr Lys Val Asn Ser Lys Leu Ser
        515                 520                 525

Leu Phe Phe Glu Ile Lys Ser
530                 535

<210> SEQ ID NO 2
<211> LENGTH: 1611
<212> TYPE: DNA
<213> ORGANISM: Artificial Sequence
<220> FEATURE:
<223> OTHER INFORMATION: Codon Optimized

<400> SEQUENCE: 2
ggcgccgacg atgtggtgga tagcagcaag agcttcgtga tggagaattt tagcagctac      60
```

```
cacggcacca aaccgggcta cgtggacagc atccagaagg gtattcagaa accgaaaagc      120
ggcacccagg gcaactatga cgatgactgg aaagaatttt acagcaccga caacaaatac      180
gatgccgccg gttatagcgt ggataatgag aatccgctga gcggcaaagc cggtggtgtt      240
gtgaaagtga cataccctgg cctgaccaag gtgctggccc tgaaggttga taacgcagag      300
accattaaga aagaactggg cctgagcctg acagaaccgc tgatggaaca ggtgggcaca      360
gaggagttca tcaagcgctt tggtgacggt gccagccgcg ttgtgctgag tctgccgttt      420
gccgaaggca gcagtagcgt ggagtacatt aacaactggg agcaggccaa agccctgagc      480
gttgagctgg agatcaactt tgagacacgc ggtaagcgtg tcaggacgc catgtacgaa       540 tatatggccc aggcctgcgc cggtaatcgt gtgcgtcgta gcgttggcag cagtctgagc      600
tgtatcaacc tggactggga cgtgatccgc gacaagacaa agaccaagat cgagagcctg      660
aaggagcatg gtcctattaa aaataagatg agcgaaagcc cgaataaaac cgttagtgaa      720
gaaaaagcca acagtatct ggaagagttt catcagaccg ccctggaaca cccggagctg       780
agtgaactga agaccgtgac cggtacaaac ccggtgtttg caggtgccaa ctatgccgca      840
tgggcagtta acgttgccca ggttatcgac agcgaaacag ccgataacct ggaaaagacc      900
accgcagccc tgagcatcct gcctggcatc ggtagcgtta tgggtattgc cgacggtgca      960
gtgcaccata taccgagga gattgtggcc cagagcatcg ccctgagcag tctgatggtg      1020
gcccaagcca ttccgctggt tggtgaactg gtggacatcg gttttgccgc ctacaacttc     1080
gtggagagca ttatcaacct gttccaggtg gtgcataaca gctacaaccg tccggcctat     1140
agtccgggcc acaaaaccca gccttttctg cacgatggct atgccgtgag ttggaataca     1200
gtggaggaca gtattattcg caccggcttt cagggcgaga gcggtcatga cattaaaatc     1260
accgccgaga acacaccgct gcctatcgca ggtgtgttac tgccgaccat tccgggcaag     1320
ctggatgtga acaaaagcaa gacacatatc agcgtgaatg ccgcaaaat ccgcatgcgc      1380 tgccgcgcaa tcgatggcga cgttacattt tgccgtccga aaagcccggt gtatgtgggc     1440
aacggtgtgc atgccaacct gcacgttgca ttccatcgca gcagtagtga aaaattcat       1500 agcaatgaga tcagcagcga tagcattggc gtgctgggct accagaagac cgttgatcac     1560
acaaaggtta acagcaaact gagcctgttc tttgaaatta aagttaata a                1611

<210> SEQ ID NO 3
<211> LENGTH: 1611
<212> TYPE: DNA
<213> ORGANISM: Artificial Sequence
<220> FEATURE:
<223> OTHER INFORMATION: Codon optimized

<400> SEQUENCE: 3
ggagccgatg atgtcgtcga tagtagtaag agttttgtca tggagaattt tagtagttat       60
catggaacaa agcccggata tgtcgatagt atacaaaagg gaatacaaaa gcccaagagt      120
ggaacacaag gaaattatga tgatgattgg aaggagtttt atagtacaga taataagtat      180
gatgccgccg gatatagtgt cgataatgag aatccctaa gtggaaaggc cggaggagtc       240
gtcaaggtca catatcccgg actaacaaag gtcctagccc taaggtcga taatgccgag      300 acaataaaga aggagctagg actaagtcta acagagcccc taatggagca agtcggaaca      360
gaggagttta taagagggtt tggagatgga gccagtaggg tcgtcctaag tctaccctt      420 gccgagggaa gtagtagtgt cgagtatata aataattggg agcaagccaa ggccctaagt      480
```

```
gtcgagctag agataaattt tgagacaagg ggaaagaggg gacaagatgc catgtatgag    540
tatatggccc aagcctgtgc cggaaatagg gtcaggagga gtgtcggaag tagtctaagt    600
tgtataaatc tagattggga tgtcataagg gataagacaa agacaaagat agagagtcta    660
aaggagcatg gacccataaa gaataagatg agtgagagtc ccaataagac agtcagtgag    720
gagaaggcca agcaatatct agaggagttt catcaaacag ccctagagca tcccgagcta    780
agtgagctaa agacagtcac aggaacaaat cccgtctttg ccggagccaa ttatgccgcc    840
tgggccgtca atgtcgccca agtcatagat agtgagacag ccgataatct agagaagaca    900
acagccgccc taagtatact acccggaata ggaagtgtca tgggaatagc cgatggagcc    960
gtccatcata atacagagga gatagtcgcc caaagtatag ccctaagtag tctaatggtc   1020
gcccaagcca tacccctagt cggagagcta gtcgatatag gatttgccgc ctataatttt   1080
gtcgagagta taataaatct atttcaagtc gtccataata gttataatag gcccgcctat   1140
agtcccggac ataagacaca acccttccta catgatggat atgccgtcag ttggaataca   1200
gtcgaggata gtataataag gacaggattt caaggagaga gtggacatga tataaagata   1260
acagccgaga atacacccct acccatagcc ggagtcctac tacccacaat acccggaaag   1320
ctagatgtca ataagagtaa gacacatata agtgtcaatg gaaggaagat aaggatgagg   1380
tgtagggcca tagatggaga tgtcacattt tgtaggccca agagtcccgt ctatgtcgga   1440
aatggagtcc atgccaatct acatgtcgcc tttcatagga gtagtagtga aagatacat    1500 agtaatgaga taagtagtga tagtataggga gtcctaggat atcaaaagac agtcgatcat   1560
acaaaggtca atagtaagct aagtctattt tttgagataa agagttaata a            1611

<210> SEQ ID NO 4
<211> LENGTH: 1611
<212> TYPE: DNA
<213> ORGANISM: Artificial Sequence
<220> FEATURE:
<223> OTHER INFORMATION: Codon optimized

<400> SEQUENCE: 4
ggcgccgacg acgttgtcga cagctccaaa tccttcgtta tggagaactt ctcttcttat     60
catggtacca aaccaggcta cgtggactcc attcagaaag gcatccagaa accaaaatca    120
ggcacgcagg gcaactatga cgacgactgg aaagagttct actccacgga caacaaatac    180
gatgcggctg gttactcggt ggacaacgaa acccgctgtc cggtaaagc gggcggtgtt     240 gtcaaagtta cctatccggg tctgaccaag gttctggcgc tgaaggttga taacgctgag    300
actatcaaaa aagagctggg cctgtccctc acggagccgc tgatggagca ggttggcact    360
gaagaattca ttaaacgctt cggtgacggc gccagccgcg tggttctgtc cctgccgttc    420
gccgaaggct cttccagtgt ggaatatatc aataactggg aacaggctaa ggctctgtcc    480
gtagaactgg aaatcaactt cgaaacgcgt ggcaaacgtg gtcaggatgc tatgtatgaa    540
tacatggcac aggcttgtgc aggtaaccgt gtacgccgtt ctgtagggtc gtctctctca    600
tgtattaacc tggactggga cgtgatccgc gataaaacca aaaccaagat cgaatctctg    660
aaagagcatg gccgatcaa aaacaagatg tctgagagcc taacaaaaac cgttctgaa     720 gagaaagcca acaatatctg gaagaattca caccaaaccg cactggaaca cccggagctg    780
tctgaactga aaactgtgac cggcacgaac ccggtgtttg cgggtgctaa ttatgccgca    840
tgggcagtga acgttgcaca ggtaatcgac agcgaaaccg ctgataacct ggaaaaaacc    900
accgcggcac tgagcatcct gccggggata ggcagcgtaa tgggtatcgc ggacggtgcg    960
```

| | |
|---|---|
| gtacaccaca acaccgaaga aattgttgcc caaagtatcg cactatcttc cctgatggta | 1020 |
| gcgcaggcca tcccgctggt tggtgaactg gtggacattg gctttgcagc ctataacttc | 1080 |
| gtagaatcca tcatcaacct tttccaggtt gtccacaaca gctacaaccg tccggcatac | 1140 |
| tctccgggtc ataaaaccca gccgttcctg catgatggtt acgctgtatc ttggaacacc | 1200 |
| gtcgaggatt cgatcattcg tactggtttc cagggcgaat ctggccacga catcaagatt | 1260 |
| actgctgaaa acaccccgct gccgatcgca ggcgttctgc tgccgaccat cccgggtaaa | 1320 |
| ctggatgtga ataaatcgaa aacccatatc tctgttaacg gccgcaaaat tcgcatgcgc | 1380 |
| tgtcgtgcga tcgatggcga tgttaccttc tgtcgtccga atccccggt gtatgtcggt | 1440 |
| aacggcgtcc atgctaatct gcatgtggcc ttccatcgct ccagctctga aaagattcac | 1500 |
| tctaacgaga tctcctccga ttctatcggc gttttgggtt accagaaaac ggtagatcac | 1560 |
| acgaaagtga acagtaaact agcctgtttt ttcgagatca aatcataata a | 1611 |

<210> SEQ ID NO 5
<211> LENGTH: 1611
<212> TYPE: DNA
<213> ORGANISM: Artificial Sequence
<220> FEATURE:
<223> OTHER INFORMATION: Codon optimized

<400> SEQUENCE: 5

| | |
|---|---|
| ggcgccgacg acgtcgtcga ctcctccaag tccttcgtca tggagaactt ctcctcctat | 60 |
| cacggcacca gcccggcta tgtcgactcc atccagaagg gcatccagaa gcccaagtcc | 120 |
| ggcacccagg gcaactatga cgacgactgg aaggagttct attccaccga caacaagtat | 180 |
| gacgccgccg gctattccgt cgacaacgag aaccccctgt ccggcaaggc cggcggcgtc | 240 |
| gtcaaggtca cctatcccgg cctgaccaag gtcctggccc tgaaggtcga caacgccgag | 300 |
| accatcaaga aggagctggg cctgtccctg accgagcccc tgatggagca ggtcggcacc | 360 |
| gaggagttca tcaagcggtt cggcgacggc gcctcccggg tcgtcctgtc cctgccttc | 420 |
| gccgagggct cctcctccgt cgagtatatc aacaactggg agcaggccaa ggccctgtcc | 480 |
| gtcgagctgg agatcaactt cgagacccgg ggcaagcggg gccaggacgc catgtatgag | 540 |
| tatatggccc aggcctgcgc cggcaaccgg gtccggcggt ccgtcggctc ctccctgtcc | 600 |
| tgcatcaacc tggactggga cgtcatccgg gacaagacca agaccaagat cgagtccctg | 660 |
| aaggagcacg gccccatcaa gaacaagatg tccgagtccc caacaagac cgtctccgag | 720 |
| gagaaggcca agcagtatct ggaggagttc accagaccg ccctggagca ccccgagctg | 780 |
| tccgagctga agaccgtcac cggcaccaac cccgtcttcg ccggcgccaa ctatgccgcc | 840 |
| tgggccgtca acgtcgccca ggtcatcgac tccgagaccg ccgacaacct ggagaagacc | 900 |
| accgccgccc tgtccatcct gccggcatc ggctccgtca tgggcatcgc cgacggcgcc | 960 |
| gtccaccaca acaccgagga gatcgtcgcc cagtccatcg ccctgtcctc cctgatggtc | 1020 |
| gcccaggcca tccccctggt cggcgagctg gtcgacatcg gcttcgccgc ctataacttc | 1080 |
| gtcgagtcca tcatcaacct gttccaggtc gtccacaact cctataaccg gcccgcctat | 1140 |
| tcccccggcc acaagaccca gcccttcctg cacgacggct atgccgtctc ctggaacacc | 1200 |
| gtcgaggact ccatcatccg gaccggcttc cagggcgagt ccggccacga catcaagatc | 1260 |
| accgccgaga caccccct gcccatcgcc ggcgtcctgc tgcccaccat ccccggcaag | 1320 |
| ctggacgtca acaagtccaa gacccacatc tccgtcaacg gccggaagat ccggatgcgg | 1380 |

| | |
|---|---|
| tgccgggcca tcgacggcga cgtcaccttc tgccggccca agtccccgt ctatgtcggc | 1440 |
| aacggcgtcc acgccaacct gcacgtcgcc ttccaccggt cctcctccga gaagatccac | 1500 |
| tccaacgaga tctcctccga ctccatcggc gtcctgggct atcagaagac cgtcgaccac | 1560 |
| accaaggtca actccaagct gtccctgttc ttcgagatca gtcctaata a | 1611 |

<210> SEQ ID NO 6
<211> LENGTH: 1611
<212> TYPE: DNA
<213> ORGANISM: Artificial Sequence
<220> FEATURE:
<223> OTHER INFORMATION: Codon optimized

<400> SEQUENCE: 6

| | |
|---|---|
| ggggcggacg acgtggtgga cagcagcaag agcttcgtga tggagaactt cagcagctac | 60 |
| cacgggacga agccggggta cgtggacagc atccagaagg ggatccagaa gccgaagagc | 120 |
| gggacgcagg ggaactacga cgacgactgg aaggagttct acagcacgga caacaagtac | 180 |
| gacgcggcgg ggtacagcgt ggacaacgag aacccgctga cgggaaggc ggggggggtg | 240 |
| gtgaaggtga cgtacccggg gctgacgaag gtgctggcgc tgaaggtgga caacgcggag | 300 |
| acgatcaaga aggagctggg gctgagcctg acggagccgc tgatggagca ggtggggacg | 360 |
| gaggagttca tcaagcggtt cggggacggg gcgagccggg tggtgctgag cctgccgttc | 420 |
| gcggagggga gcagcagcgt ggagtacatc aacaactggg agcaggcgaa ggcgctgagc | 480 |
| gtggagctgg agatcaactt cgagacgcgg gggaagcggg ggcaggacgc gatgtacgag | 540 |
| tacatggcgc aggcgtgcgc ggggaaccgg gtgcggcgga cgtggggag cagcctgagc | 600 |
| tgcatcaacc tggactggga cgtgatccgg gacaagacga agacgaagat cgagagcctg | 660 |
| aaggagcacg gccgatcaa gaacaagatg agcgagagcc cgaacaagac ggtgagcgag | 720 |
| gagaaggcga agcagtacct ggaggagttc caccagacgg cgctggagca cccggagctg | 780 |
| agcgagctga gacggtgac ggggacgaac ccggtgttcg cggggggcgaa ctacgcggcg | 840 |
| tgggcggtga cgtggcgca ggtgatcgac agcgagacgg cggacaacct ggagaagacg | 900 |
| acggcggcgc tgagcatcct gccggggatc gggagcgtga tggggatcgc ggacggggcg | 960 |
| gtgcaccaca cacggagga gatcgtggcg cagagcatcg cgctgagcag cctgatggtg | 1020 |
| gcgcaggcga tcccgctggt gggggagctg gtggacatcg ggttcgcggc gtacaacttc | 1080 |
| gtggagagca tcatcaacct gttccaggtg gtgcacaaca gctacaaccg gccggcgtac | 1140 |
| agcccggggc acaagacgca gccgttcctg cacgacgggt acgcggtgag ctggaacacg | 1200 |
| gtggaggaca gcatcatccg gacgggttc caggggggaga gcgggcacga catcaagatc | 1260 |
| acggcggaga acacgccgct gccgatcgcg ggggtgctgc tgccgacgat cccggggaag | 1320 |
| ctggacgtga acaagagcaa gacgcacatc agcgtgaacg gcggaagat ccggatgcgg | 1380 |
| tgccgggcga tcgacgggga cgtgacgttc tgccggccga agagcccggt gtacgtgggg | 1440 |
| aacgggtgc acgcgaacct gcacgtggcg ttccaccgga gcagcagcga gaagatccac | 1500 |
| agcaacgaga tcagcagcga cagcatcggg gtgctggggt accagaagac ggtggaccac | 1560 |
| acgaaggtga acagcaagct gagcctgttc ttcgagatca gagctaata a | 1611 |

<210> SEQ ID NO 7
<211> LENGTH: 1611
<212> TYPE: DNA
<213> ORGANISM: Artificial Sequence
<220> FEATURE:
<223> OTHER INFORMATION: Codon optimized

<400> SEQUENCE: 7

```
ggtgcggacg acgttgttga ctcttctaaa tctttcgtta tggaaaactt ctcttcttac      60
cacggtacca aaccgggtta cgttgactct atccagaaag gtatccagaa accgaaatct    120
ggtacccagg gtaactacga cgacgactgg aaagaattct actctaccga caacaaatac    180
gacgcggcgg ttactctgt tgacaacgaa aaccgctgt ctggtaaagc gggtggtgtt      240
gttaaagtta cctacccggg tctgaccaaa gttctggcgc tgaaagttga caacgcggaa    300
accatcaaaa agaactggg tctgtctctg accgaaccgc tgatggaaca ggttggtacc     360
gaagaattca tcaaacgttt cggtgacggt gcgtctcgtg ttgttctgtc tctgccgttc    420
gcggaaggtt cttcttctgt tgaatacatc aacaactggg aacaggcgaa agcgctgtct    480
gttgaactgg aaatcaactt cgaaacccgt ggtaaacgtg tcaggacgc gatgtacgaa     540
tacatggcgc aggcgtgcgc gggtaaccgt gttcgtcgtt ctgttggttc ttctctgtct    600
tgcatcaacc tggactggga cgttatccgt gacaaaacca aaaccaaaat cgaatctctg    660
aaagaacacg gtccgatcaa aaacaaaatg tctgaatctc gaacaaaac cgtttctgaa     720
gaaaaagcga acagtacct ggaagaattc accagaccg cgctggaaca cccggaactg      780
tctgaactga aaccgttac cggtaccaac ccggttttcg cgggtgcgaa ctacgcggcg     840
tgggcggtta cgttgcgca ggttatcgac tctgaaaccg cggacaacct ggaaaaaacc    900
accgcggcgc tgtctatcct gccgggtatc ggttctgtta tgggtatcgc ggacggtgcg    960
gttcaccaca caccgaaga atcgttgcg cagtctatcg cgctgtcttc tctgatggtt    1020
gcgcaggcga tcccgctggt tggtgaactg gttgacatcg gtttcgcggc gtacaacttc    1080
gttgaatcta tcatcaacct gttccaggtt gttcacaact cttacaaccg tccggcgtac    1140
tctccgggtc acaaaaccca gccgttcctg cacgacggtt acgcggtttc ttggaacacc    1200
gttgaagact ctatcatccg taccggtttc cagggtgaat ctggtcacga catcaaaatc    1260
accgcggaaa acacccgct gccgatcgcg ggtgttctgc tgccgaccat cccgggtaaa    1320
ctggacgtta caaatctaa aacccacatc tctgttaacg tcgtaaaat ccgtatgcgt    1380
tgccgtgcga tcgacggtga cgttaccttc tgccgtccga atctccggt ttacgttggt    1440
aacggtgttc acgcgaacct gcacgttgcg ttccaccgtt cttcttctga aaaaatccac    1500
tctaacgaaa tctcttctga ctctatcggt gttctgggtt accagaaaac cgttgaccac    1560
accaaagtta actctaaact gtctctgttc ttcgaaatca atcttaata a             1611
```

<210> SEQ ID NO 8
<211> LENGTH: 1611
<212> TYPE: DNA
<213> ORGANISM: Artificial Sequence
<220> FEATURE:
<223> OTHER INFORMATION: Codon optimized

<400> SEQUENCE: 8

```
ggcgccgacg acgtcgtcga ctcctccaag tccttcgtca tggagaactt ctcctcctat     60
cacggcacca agcccggcta tgtcgactcc atccagaagg gcatccagaa gcccaagtcc    120
ggcacccagg gcaactatga cgacgactgg aaggagttct attccaccga caacaagtat    180
gacgccgccg ctattccgt cgacaacgag aaccccctgt ccggcaaggc cggcggcgtc    240
gtcaaggtca cctatcccgg cctgaccaag gtcctggccc tgaaggtcga caacgccgag    300
accatcaaga aggagctggg cctgtccctg accgagcccc tgatggagca ggtcggcacc    360
```

| | |
|---|---|
| gaggagttca tcaagcggtt cggcgacggc gcctcccggg tcgtcctgtc cctgcccttc | 420 |
| gccgagggct cctcctccgt cgagtatatc aacaactggg agcaggccaa ggccctgtcc | 480 |
| gtcgagctgg agatcaactt cgagacccgg ggcaagcggg ccaggacgc catgtatgag | 540 |
| tatatggccc aggcctgcgc cggcaaccgg gtccggcggt ccgtcggctc ctccctgtcc | 600 |
| tgcatcaacc tggactggga cgtcatccgg acaagacca agaccaagat cgagtccctg | 660 |
| aaggagcacg gccccatcaa gaacaagatg tccgagtccc ccaacaagac cgtctccgag | 720 |
| gagaaggcca agcagtatct ggaggagttc caccagaccg ccctggagca ccccgagctg | 780 |
| tccgagctga gaccgtcac cggcaccaac cccgtcttcg ccggcgccaa ctatgccgcc | 840 |
| tgggccgtca acgtcgccca ggtcatcgac tccgagaccg ccgacaacct ggagaagacc | 900 |
| accgccgccc tgtccatcct gcccggcatc ggctccgtca tgggcatcgc cgacggcgcc | 960 |
| gtccaccaca acaccgagga gatcgtcgcc cagtccatcg ccctgtcctc cctgatggtc | 1020 |
| gcccaggcca tccccctggt cggcgagctg gtcgacatcg gcttcgccgc ctataacttc | 1080 |
| gtcgagtcca tcatcaacct gttccaggtc gtccacaact cctataaccg gcccgcctat | 1140 |
| tcccccggcc acaagaccca gcccttcctg cacgacggct atgccgtctc ctggaacacc | 1200 |
| gtcgaggact ccatcatccg gaccggcttc cagggcgagt ccggcacga catcaagatc | 1260 |
| accgccgaga cacccccct gcccatcgcc ggcgtcctgc tgcccaccat ccccggcaag | 1320 |
| ctggacgtca caagtccaa gacccacatc tccgtcaacg gccggaagat ccggatgcgg | 1380 |
| tgccgggcca tcgacggcga cgtcaccttc tgccggccca gtccccccgt ctatgtcggc | 1440 |
| aacggcgtcc acgccaacct gcacgtcgcc ttccaccggt cctcctccga gaagatccac | 1500 |
| tccaacgaga tctcctccga ctccatcggc gtcctgggct atcagaagac cgtcgaccac | 1560 |
| accaaggtca actccaagct gtccctgttc ttcgagatca gtcctaata a | 1611 |

<210> SEQ ID NO 9
<211> LENGTH: 1611
<212> TYPE: DNA
<213> ORGANISM: Artificial Sequence
<220> FEATURE:
<223> OTHER INFORMATION: Codon optimized

<400> SEQUENCE: 9

| | |
|---|---|
| ggcgccgacg acgtcgtcga ctcctccaag tccttcgtca tggagaactt ctcctcctat | 60 |
| cacggcacca agcccggcta tgtcgactcc atccagaagg gcatccagaa gcccaagtcc | 120 |
| ggcacccagg gcaactatga cgacgactgg aaggagttct attccaccga caacaagtat | 180 |
| gacgccgccg gctattccgt cgacaacgag aaccccctgt ccggcaaggc cggcggcgtc | 240 |
| gtcaaggtca cctatcccgg cctgaccaag gtcctggccc tgaaggtcga caacgccgag | 300 |
| accatcaaga aggagctggg cctgtccctg accgagcccc tgatggagca ggtcggcacc | 360 |
| gaggagttca tcaagcggtt cggcgacggc gcctcccggg tcgtcctgtc cctgcccttc | 420 |
| gccgagggct cctcctccgt cgagtatatc aacaactggg agcaggccaa ggccctgtcc | 480 |
| gtcgagctgg agatcaactt cgagacccgg ggcaagcggg ccaggacgc catgtatgag | 540 |
| tatatggccc aggcctgcgc cggcaaccgg gtccggcggt ccgtcggctc ctccctgtcc | 600 |
| tgcatcaacc tggactggga cgtcatccgg acaagacca agaccaagat cgagtccctg | 660 |
| aaggagcacg gccccatcaa gaacaagatg tccgagtccc ccaacaagac cgtctccgag | 720 |
| gagaaggcca agcagtatct ggaggagttc caccagaccg ccctggagca ccccgagctg | 780 |
| tccgagctga gaccgtcac cggcaccaac cccgtcttcg ccggcgccaa ctatgccgcc | 840 |

```
tgggccgtca acgtcgccca ggtcatcgac tccgagaccg ccgacaacct ggagaagacc        900
accgccgccc tgtccatcct gcccggcatc ggctccgtca tgggcatcgc cgacggcgcc        960
gtccaccaca acaccgagga gatcgtcgcc cagtccatcg ccctgtcctc cctgatggtc       1020
gcccaggcca tcccctggt cggcgagctg gtcgacatcg gcttcgccgc ctataacttc        1080
gtcgagtcca tcatcaacct gttccaggtc gtccacaact cctataaccg gcccgcctat       1140
tcccccggcc acaagaccca gcccttcctg cacgacggct atgccgtctc ctggaacacc       1200
gtcgaggact ccatcatccg gaccggcttc cagggcgagt ccggccacga catcaagatc       1260
accgccgaga cacccccct gcccatcgcc ggcgtcctgc tgcccaccat ccccggcaag        1320
ctggacgtca acaagtccaa gacccacatc tccgtcaacg gccggaagat ccggatgcgg       1380
tgccgggcca tcgacggcga cgtcaccttc tgccggccca gtcccccgt ctatgtcggc        1440
aacggcgtcc acgccaacct gcacgtcgcc ttccaccggt cctcctccga agatccac         1500
tccaacgaga tctcctccga ctccatcggc gtcctgggct atcagaagac cgtcgaccac       1560
accaaggtca actccaagct gtccctgttc ttcgagatca agtcctaata a                1611
```

<210> SEQ ID NO 10
<211> LENGTH: 1611
<212> TYPE: DNA
<213> ORGANISM: Artificial Sequence
<220> FEATURE:
<223> OTHER INFORMATION: Codon optimized

<400> SEQUENCE: 10

```
ggtgctgacg acgttgttga ctcttctaaa tctttcgtta tggaaaactt ctcttcttac         60
cacggtacca aaccgggtta cgttgactct atccagaaag gtatccagaa accgaaatct        120
ggtacccagg gtaactacga cgacgactgg aagaattct actctaccga caacaaatac        180
gacgctgctg gttactctgt tgacaacgaa aaccgctgt ctggtaaagc tggtggtgtt         240
gttaaagtta cctacccggg tctgaccaaa gttctggctc tgaaagttga caacgctgaa        300
accatcaaaa agaactggg tctgtctctg accgaaccgc tgatggaaca ggttggtacc         360
gaagaattca tcaaacgttt cggtgacggt gcttctcgtg ttgttctgtc tctgccgttc        420
gctgaaggtt cttcttctgt tgaatacatc aacaactggg aacaggctaa agctctgtct        480
gttgaactgg aaatcaactt cgaaacccgt ggtaaacgtg tcaggacgc tatgtacgaa         540
tacatggctc aggcttgcgc tggtaaccgt gttcgtcgtt ctgttggttc ttctctgtct        600
tgcatcaacc tggactggga cgttatccgt gacaaaacca aaaccaaaat cgaatctctg        660
aaagaacacg gtccgatcaa aaacaaaatg tctgaatctc cgaacaaaac cgttctgaa         720
gaaaagcta acagtacct ggaagaattc accagaccg ctctggaaca cccggaactg           780
tctgaactga aaaccgttac cggtaccaac ccggttttcg ctggtgctaa ctacgctgct        840
tgggctgtta acgttgctca ggttatcgac tctgaaaccg ctgacaacct ggaaaaaacc       900
accgctgctc tgtctatcct gccgggtatc ggttctgtta tgggtatcgc tgacggtgct       960
gttcaccaca cacccgaaga aatcgttgct cagtctatcg ctctgtcttc tctgatggtt      1020
gctcaggcta tcccgctggt tggtgaactg gttgacatcg gttttcgctgc ttacaacttc     1080
gttgaatcta tcatcaacct gttccaggtt gttcacaact cttacaaccg tccggcttac      1140
tctccgggtc acaaaaccca gccgttcctg cacgacggtt acgctgtttc ttggaacacc      1200
gttgaagact ctatcatccg taccggtttc cagggtgaat ctggtcacga catcaaaatc      1260
```

```
accgctgaaa acaccccgct gccgatcgct ggtgttctgc tgccgaccat cccgggtaaa    1320
ctggacgtta acaaatctaa aacccacatc tctgttaacg gtcgtaaaat ccgtatgcgt    1380
tgccgtgcta tcgacggtga cgttaccttc tgccgtccga atctccggt ttacgttggt     1440 aacggtgttc acgctaacct gcacgttgct ttccaccgtt cttcttctga aaaaatccac    1500
tctaacgaaa tctcttctga ctctatcggt gttctgggtt accagaaaac cgttgaccac    1560
accaaagtta actctaaact gtctctgttc ttcgaaatca atcttaata a              1611

<210> SEQ ID NO 11
<211> LENGTH: 17
<212> TYPE: PRT
<213> ORGANISM: Artificial Sequence
<220> FEATURE:
<223> OTHER INFORMATION: Confirmation of disulphide bonds in BErCRM197

<400> SEQUENCE: 11

Gly Gln Asp Ala Met Tyr Glu Tyr Met Ala Gln Ala Cys Ala Gly Asn
1               5                   10                  15

Arg

<210> SEQ ID NO 12
<211> LENGTH: 17
<212> TYPE: PRT
<213> ORGANISM: Artificial Sequence
<220> FEATURE:
<223> OTHER INFORMATION: Confirmation of disulphide bonds in BErCRM197

<400> SEQUENCE: 12

Ser Val Gly Ser Ser Leu Ser Cys Ile Asn Leu Asp Trp Asp Val Ile
1               5                   10                  15

Arg

<210> SEQ ID NO 13
<211> LENGTH: 10
<212> TYPE: PRT
<213> ORGANISM: Artificial Sequence
<220> FEATURE:
<223> OTHER INFORMATION: Confirmation of N-terminal sequence of rCRM197

<400> SEQUENCE: 13

Gly Ala Asp Asp Val Val Asp Ser Ser Lys
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Confirmation of disulphide bonds is BErCRM197

<400> SEQUENCE: 14

Ala Ile Asp Gly Asp Val Thr Phe Cys Arg Pro Lys
1               5                   10
```

CODON OPTIMIZED POLYNUCLEOTIDE FOR HIGH LEVEL EXPRESSION OF CRM197

TECHNICAL FIELD

This application is a 371 U.S. National Stage Application of International Patent Application No. PCT/IN2015/000427 filed Nov. 17, 2015, which claims priority to Indian Patent Application Serial No. 4045/CHE/2014 filed on Nov. 20, 2014, the entire contents of which are incorporated herein by reference and relied upon.

The present invention relates to a high level expression of bacterial toxoid by means of an optimized novel polynucleotide sequence and host transformed with the said polynucleotide.

The invention also provides a method for high production of polypeptide $CRM_{197}$ wherein, the polynucleotide of the present invention is used to transform a suitable host resulting in over-expression of corresponding proteins and a method for isolating the expressed polypeptide.

BACKGROUND

Diphtheria toxin (DT) is a protein exotoxin that is synthesized and secreted by *Corynebacterium diphtheriae*. The toxigenic strains of *Corynebacterium diphtheriae* contain a bacteriophage lysogen carrying the toxin gene. Mature form of DT is synthesized as a 535 amino-acid containing single polypeptide, which is derived from an initial 536 propeptide which undergoes proteolysis at positions 190, 192 and 193 to form the mature toxin. This splicing or proteolysis results into two subunits, A and B which are joined together by a disulfide bridge (Moskang et al Biol. Chem. 264: 15709-15713, 1989). Subunit A is catalytically active NAD-dependent ADP-ribosyl transferase portion. It is responsible for rendering Elongation Factor-2 (EF-2) inactive, and hence down regulates the protein synthesis in a target cell.

Diphtheria toxin is highly cytotoxic; a single molecule can be lethal to a cell, and a dose of 10 ng/kg can kill animals and humans. In course of providing an artificial immunity by injection of this toxoid, a process of detoxification should be included to render it safe for consumption by the recipient. Conventionally it was detoxified by chemical modification of the natural forms of DT, in such a manner that it still retains the required antigenicity required in a vaccine preparation.

Subsequently, a genetically detoxified form of Diphtheria Toxin known as Cross Reacting Material 197 or $CRM_{197}$ was introduced; which essentially retains the immunological cross-reacting properties of DT.

$CRM_{197}$ has been used in preparation of conjugate vaccines including *Corynebacterium diphtheria, Hepatitis B, Bordetella pertussis, Clostridium tetani, Neisseria menin-gitides, Streptococcus pneumonia, Haemophilus influenza*. It was generated by nitrosoguanidine mutagenesis of the toxigenic corynephage β, which was then used to infect *Corynebacterium diphtheria*. (Uchida et al Nature New Biology (1971) 233; 8-11, Nucleic Acids Res. 1984 May 25; 12(10): 4063-9)

$CRM_{197}$ has been studied for its potential use as a DT booster or vaccine antigen. The $CRM_{197}$ protein has the same molecular weight as DT; but differs in a single base change in the A subunit i.e. a base change in the polynucleotide sequence of wild type DT, wherein a replacement of Guanine to Adenine results into an amino acid substitution at position 52, resulting into glutamic acid in $CRM_{197}$ instead of glycine (Giannini G. et al., 1984). This point mutation results in a significant loss of toxicity and renders $CRM_{197}$ safe for human use.

Production of significant quantities of diphtheria toxins such as $CRM_{197}$ for use in vaccines has been hindered due to low level of expression in wild type bacteria. This problem has been addressed previously by expressing $CRM_{197}$ in *Escherichia coli* by Bishai et al., (J. Baeteriol. 189:5140-5151). who describe the expression of a recombinant fusion protein containing diphtheria toxin (including the tox signal sequence), but this led to the production of degraded protein. The low yield in active form is also associated with degradation, improper folding, or both, depending on the specific characteristics, e.g., size and secondary structure, of the toxin. Hence as with most biopharmaceuticals, there is additional loss of expressed protein that occurs during the purification steps of $CRM_{197}$, whereby maintaining a biologically active form of $CRM_{197}$ poses a challenge. Therefore, there is need to achieve high level expression of bacterial toxoid $CRM_{197}$ in an active form.

WO 2011/042516 discloses an improved process for making a bacterial toxin by periplasmic expression comprising the steps of a) growing a culture of the bacterial host cell containing an expression vector in which particular signal sequence are linked to the sequence of a bacterial toxin and b) inducing expression of the polypeptide containing particular signal sequence linked to a bacterial toxin such that a bacterial toxin is expressed periplasmically.

WO 2013/178974 A1 discloses a process for the intracellular expression of $CRM_{197}$ in an *Escherichia coli* host, comprising expressing a vector comprising a gene encoding $CRM_{197}$ operably linked to a Promoter and at feast one perfect Palindrome Operator sequence.

WO 2015/134402 A1 discloses a process for producing a recombinant $CRM_{197}$ in a reduced genome of *Escherichia coli* host comprising incubating a reduced genome *Escherichia coli* comprising an expression vector comprising a nucleotide sequence encoding a $CRM_{197}$ protein fused to a signal sequence that directs transfer of the $CRM_{197}$ protein to the periplasm operably linked to an expression control sequence under conditions suitable for the expression of the recombinant $CRM_{197}$ protein, whereby a yield of at least 1 gram per liter of soluble $CRM_{197}$ is obtained and wherein the native parent Escherichia coli strain is a 12 strain, preferably K12 MG1655.

US 2012/0128727 A1 discloses an isolated nucleic acid molecule which encodes polypeptide $CRM_{197}$, an expression vector comprising the isolated nucleic acid molecule and a method for recombinant production of a $CRM_{197}$ tag fusion protein, comprising culturing the recombinant cell under conditions favoring production of said $CRM_{197}$ tag fusion protein, and isolating said fusion protein.

US 2012/0289688 A1 discloses a process for periplasmic expression of a recombinant polypeptide by (A) Growing a culture of a gram-negative host cell; and (B) Inducing expression of a polypeptide such that a protein is expressed periplasmically; wherein one or more of the following steps is actioned during expression: (i) The pH of step a) is lower than the pH of step b); (ii). The temperature of step a) is higher than the temperature of step b); or (iii). The substrate feed rate of step a) is higher than the substrate feed rate of step b).

US 2014/0050758 A1 discloses a process for periplasmic expression of a bacterial toxoid comprising the steps of: a) growing a culture of a gram negative host cell in a fermentation medium, wherein the host cell is transformed with a polynucleotide, and wherein the polynucleotide encodes the bacterial toxoid and a periplasmic signal sequence; inducing expression of the bacterial toxoid;

b) maturing the host cell, wherein the maturing step comprises: I) subjecting the host cell to a pH shock: II) incubating the host cell with no feed addition; or III) subjecting the host cell to a temperature below −20° C.; and c) extracting the bacterial toxoid from the host cell wherein the extraction process comprises osmotic shock wherein the gram negative host cell is selected from the group consisting of *Escherichia coli*, Pseudomonas and Moraxella, wherein the host cell is alive during step b) and wherein the process is carried out in a fermenter which contains 10-5000 liters of culture.

U.S. Pat. No. 8,530,171 discloses a method for producing a recombinant toxin protein in a Pseudomonas host cell, said method comprising: ligating into an expression vector a nucleotide sequence encoding the toxin protein; transforming the Pseudomonas host cell with the expression vector; and culturing the transformed Pseudomonas host cell in a culture media suitable for the expression of the recombinant toxin protein; wherein the recombinant carrier protein is $CRM_{197}$, and wherein the recombinant protein is produced at a yield of soluble or active $CRM_{197}$ protein of about 0.2 grams per liter to about 12 grams per liter.

Conjugated polysaccharide vaccines that use $CRM_{197}$ as a carrier protein have been approved for human use. These include: MENVEO® (Meningococcal (Groups A, C, Y, and W-135) Oligosaccharide Diphtheria $CRM_{197}$ Conjugate Vaccine) (Novartis Vaccines and Diagnostics), a vaccine indicated for preventing invasive meningococcal disease caused by *Neisseria meningitidis* subgroups A, C, Y, and W-135; MENJUGATE® (Meningococcal Group C-$CRM_{197}$ Conjugate Vaccine) (Novartis Vaccines and Diagnostics), a meningococcal group C conjugate vaccine; and PREVNAR® (Pneumococcal 7-valent Conjugate Vaccine (Diphtheria $CRM_{197}$ Protein)) (Wyeth Pharmaceuticals, Inc.), a childhood pneumonia vaccine that targets thirteen serotypes of *Streptococcus pneumoniae*, and HIBTITER® (Haemophilus b Conjugate Vaccine (Diphtheria $CRM_{197}$ Protein Conjugate)) (Wyeth), a *Haemophilus influenzae* type b vaccine. In addition, $CRM_{197}$ has potential use as a boosting antigen for *C. diphtheria* vaccination and is being investigated as a carrier protein for use in other vaccines.

There has recently been a growing interest in $CRM_{197}$ because of its potential antitumor action relating to its capacity to bind the soluble form of HB-EGF (Mekada et al, US Patent Publication NO. 2006/0270600A1). This antitumor function is attributable not only to $CRM_{197}$, but also to other non-toxic derivatives of the DT toxin (e.g. the double mutant DT52E148K, or the fusion protein GST-DT). These mutants have been constructed by PGR, starting from the gene encoding $CRM_{197}$. In said studies, however, the whole $CRM_{197}$ was produced using cultures of *C. diphtheria*, grown at 35° C. for 16-17 hours. The CRMw was purified from the supernatant by means of an initial precipitation with ammonium sulphate, followed by three successive steps in ion exchange and hydrophobic chromatography (Mekada et al.).

Hence, there is an evident need for an alternative method for the production of $CRM_{197}$ with high yield and cost-effective manner. Therefore, a method for economically producing $CRM_{197}$ would greatly facilitate vaccine research, development and manufacturing.

Objective of the Invention

The main objective of the present intention is to provide an optimized polynucleotide for high level expression of $CRM_{197}$.

Yet another objective is to provide a tunable process for controlling the expression of polypeptide as to obtain $CRM_{197}$.

Yet another objective is to provide a high level expression process for commercial production of $CRM_{197}$ in pure form with high yield.

SUMMARY

The present invention provides an optimized polynucleotide sequence comprising of SEQ ID NO. 2 and its variants which are at least 70% homologous to the said optimized polynucleotide sequence SEQ ID NO. 2.

In another embodiment, the present invention provides an optimized polynucleotide sequence (SEQ ID NO. 2) and its structural variants selected from but not limited to SEQ ID NO. 3, 4, 5, 6, 7, 8, 9 and 10 useful for high level expression of polypeptide In yet another embodiment, the present invention provides an optimized polynucleotide sequence (SEQ ID NO. 2) and its variants like SEQ ID NO. 3, 4, 5, 6, 7, 8, 9 and 10 which are at least 70 to 88% homologous to the said optimized polynucleotide sequence SEQ ID NO. 2.

The present invention further provides a process for the production of polypeptide, comprising steps of:

a) selecting an optimized polynucleotide sequence essentially consisting of SEQ ID NO. 2 or its variants which are at least 70% homologous to SEQ ID NO. 2, b) optionally ligating the polynucleotide sequences of step (a) into a suitable vector, c) inserting or transforming the polynucleotide sequence into *Escherichia coli* host cell, d) culturing the transformed host cell in a culture media for high level expression of the polypeptide, e) maintaining the induction temperature between 10 to 40° C. to produce polypeptide, f) extracting the bacterial polypeptide from the host cell, followed by purification to obtain pure polypeptide with high yields.

The polypeptide obtained above is suitably used as a carrier protein for preparation of conjugated immunogenic preparations.

DETAILED DESCRIPTION

Figure 1:
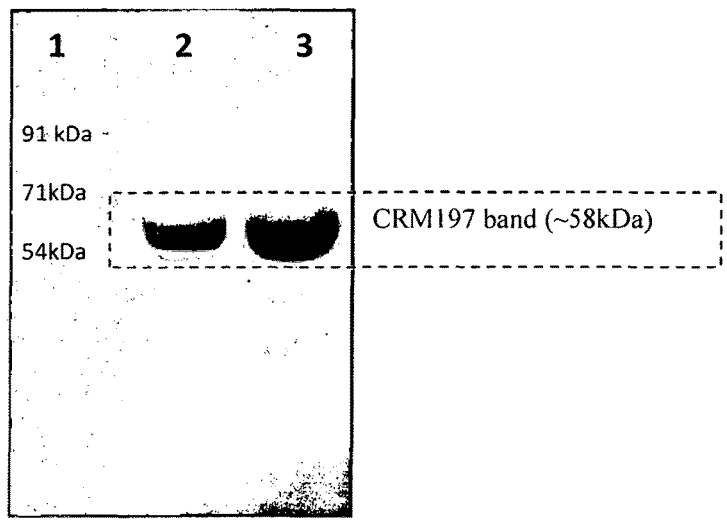
FIG. 1: illustrates SDS-PAGE electrophoretic gel run corresponding to the expressed $CRM_{197}$ which is encoded by polynucleotide SEQ ID NO. 2; where Lane 1; Standard Molecular Mass Marker; Lane 2 and 3; $CRM_{197}$ which was separated and purified form the total cellular proteins of *E. coli* culture extracts and run on non-reducing and reducing SDS-PAGE, respectively.
Figure 2:
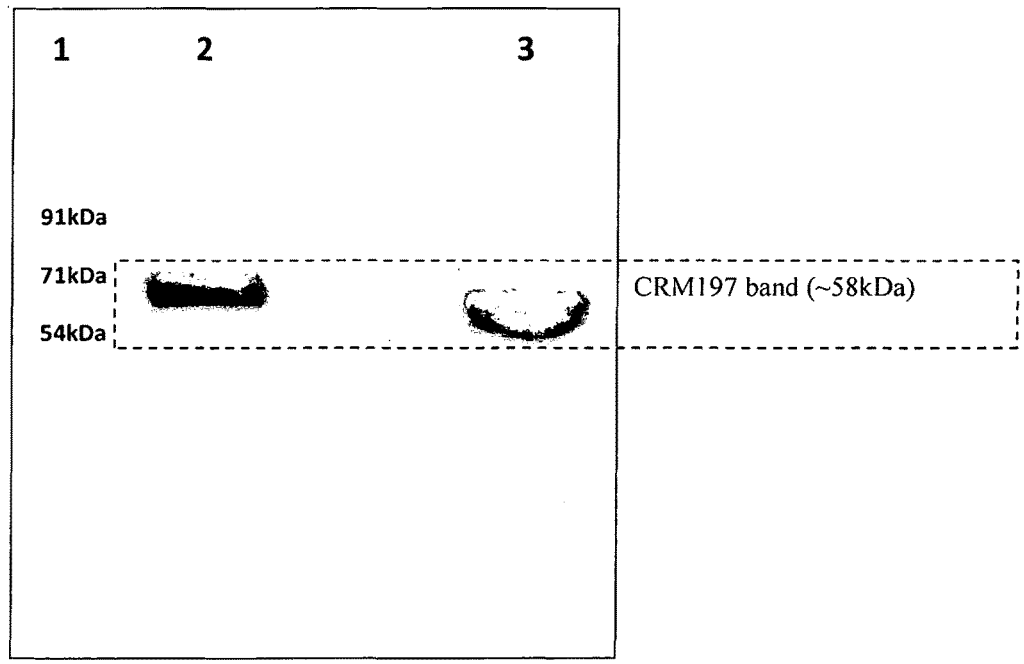
FIG. 2: illustrates western blot analysis of purified $CRM_{197}$ using rabbit polyclonal antibodies; Lane 1: Molecular weight ladder. Lane: 2 and 3 includes $CRM_{197}$ samples etectrophoresed under reducing and non-reducing conditions, respectively.
Figure 3:
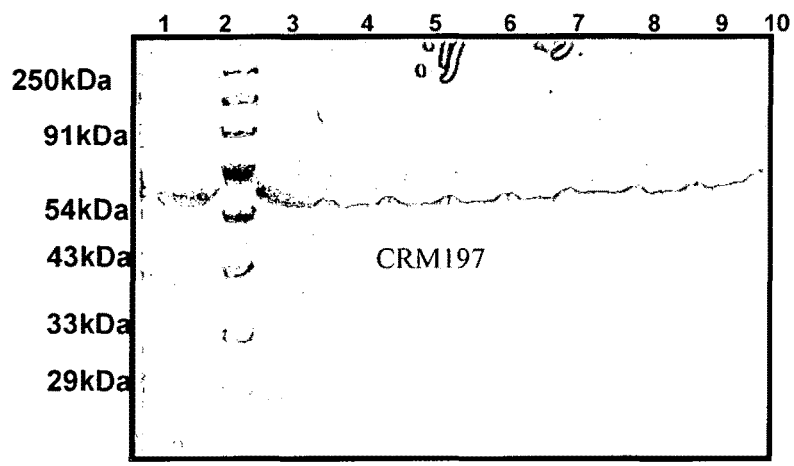
FIG. 3: SDS PAGE shows purified soluble fraction Lane 1: Reference protein; Lane 2: protein molecular weight marker; Lane 3-10: Pooled Polypeptide $CRM_{197}$.
Figure 4:
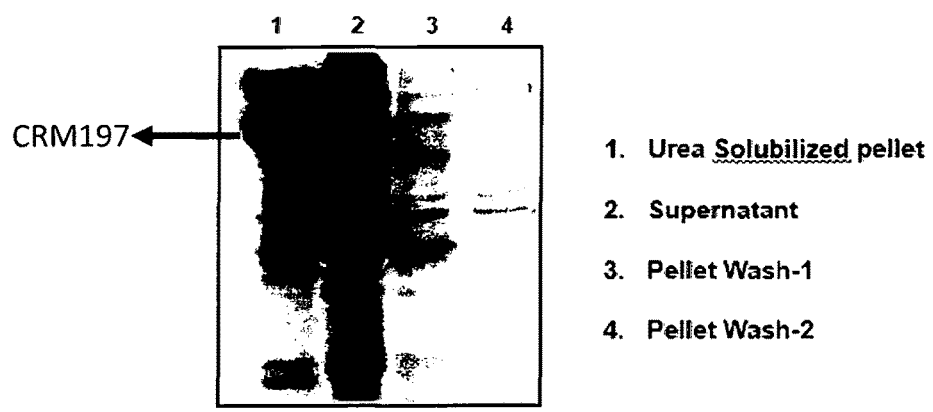
FIG. 4: Electrophoretic gel run (SDS PAGE 12%) showing test conducted on solubilization of $CRM_{197}$, Lane 1: Urea solubilized fraction of $CRM_{197}$; Lane 2: Supernatant; Lane 3: Sample from first pellet wash; Lane 4: Sample pooled from $2^{nd}$ pellet wash.

The polypeptide expression for use as pharmaceutical product or vaccines requires achieving high biomass and/or productivity of the host cell line. The efficiency of polypeptide production can be significantly diminished in absence of multiple factors, which includes use of an optimal polynucleotide sequence encoding that polypeptide. The genetic code is known to exhibit degeneracy, which amounts to the variance in the polynucleotide sequence encoding the same amino acid sequence. The rate of synthesis of amino acid chain is a determinant factor in the overall expression levels from an individual gene, which effect the design of the expression construct, is of high significance. Thus the construction of an optimal polynucleotide sequence is important in determining the overall expression levels of a polypeptide and has to be well regulated. It includes, but is not limited to the frequency with which the codons are preferred in an organism or in case of artificial vehicles or vectors, the nearest frequency desired. This in turn reflects tRNA abundance or the cognate cellular tRNA frequencies from which the synonymous codon choice patterns has to be carefully selected. Additional factors also include the potential for formation of secondary structures, mRNA levels and RNA stability, subsequent intended manipulations to be carried out, synthesis routes and so on. The occurrence of these structures has to be carefully regulated as the choice of these patterns differs with the optimizations for individual protein of interest and expression hosts.

Accordingly, the main embodiment of the present invention provides an optimized polynucleotide sequence (SEQ ID NO. 2) and its structural variants.

In another embodiment, the invention provides an optimized polynucleotide sequence (SEQ ID NO. 2) and its structural variants selected from but not limited to SEQ ID NO. 3, 4, 5, 6, 7, 8, 9 and 10 having equal to or more than 70% similarity useful for high level expression of polypeptide for $CRM_{197}$.

Periplasmic expression refers to the secretion of the expressed product from the intended gene of interest (such as a bacterial toxoid or Diphtheria Toxoid) in the periplasmic space within a host cell.

Cytoplasmic expression refers to the expression of protein in the cytoplasmic compartment of the cell, enclosed within cell membrane.

Induction of expression refers to the step performed to induce the expression from the polynucleotide so that the product is obtained at an accelerated rate, this may involve addition of suitable inducing agent such as IPTG, arabinose. maltose and the like.

The optimized sequence of the present invention is applicable to Other variants of SEQ ID NO. 2 selected from but not limited to SEQ ID NO. 3, 4, 5, 6, 7, 8, 9, 10 and also include sequences in the production of derivatives of SEQ ID NO. 1, wild type Diphtheria toxin which retains the same inflammatory and immunostimulatory properties and is capable of binding to the cell receptor HB-EGF, but differs from $CRM_{197}$ in a single amino acid substitution and lack of cellular toxicity on target host.

The polynucleotide sequence of the $CRM_{197}$ may be derived from the sequence of Diphtheria Toxin (Greenfield, L. et al., 1983, Proc. Natl. Acad. Sci. USA 80:6853-6857), or by using the amino acid sequence of $CRM_{197}$ given by Giannini G. et al, (1984) as reference. The wild type polynucleotide sequence thus obtained was optimized for high expression in the host cell, more preferably Gram negative cell, more preferably *Escherichia coli* as host cell. Such a polynucleotide sequence of the present invention can be prepared by chemical synthesis or by means of an assembly procedure.

In yet another embodiment there is provided a process for the intracellular expression of $CRM_{197}$ in a host cell wherein an expression construct with regulatory sequence provides for the expression of the polynucleotide of the invention. This polynucleotide sequence may be associated with a signal sequence for directed transport of the encoded polypeptide. It may be operably linked to periplasmic signal sequence which provides the expression targeted to be secreted in the periplasmic space of the host.

The present invention also provides high level production of $CRM_{197}$, wherein periplasmic expression is brought about by providing a suitable induction temperature for the expression of polynucleotide, without any heterologous sequence for directed transport into the periplasmic space.

Optionally the polynucleotide of the invention may also be associated with polynucleotides of tag polypeptides. The presence of a tag is also known to enhance the stability and solubility of the protein in the cytoplasm and for its subsequent purification.

These tags can be associated at 5' terminus or 3' terminus, singly or in combination pertinent to multi-tagging, with an oligonucleotide sequence that encodes a tag polypeptide to facilitate its cytoplasmic stability and/or subsequent purification using matrices and resins with a high affinity for the various tag peptides. Various tags which cap. be used according to the invention include HA Tags (hemagglutinin), MYC Tag, Strep II, FLAG, HPC (heavy chain of protein C), glutathione-S-transferase (GST), maltose-binding protein (MBP), cellulose-binding protein (CBD) and chitin-binding protein (CBP).

The polynucleotide of invention may also be incorporated in a vector construct comprising regulatory sequence, with molecular techniques well known in art (See Sambrook et al, Molecular Cloning, 2nd ed., (1989)). This includes but is not limited to, a suitable promoter, origin of replication, ribosomal binding site, transcription termination sequence, selectable markers and multiple cloning site. In particular, a plasmid with an efficient and specific construct is preferred; such as one including T7 Promoter specific for RNA polymerase enzyme of the phage T7. Such methods may be referred to but are not limited to one disclosed in U.S. Patent Application NO. 2012/0128727; U.S. Pat. No. 5,055,294; U.S. Pat. No. 5,128,130: U.S. Pat. No. 5,281,532; U.S. Pat. No. 4,695,455; U.S. Pat No. 4,861,595; U.S. Pat. No. 4,755,465 and U.S. Pat. No. 5,169,760. A plasmid system for producing $CRM_{197}$ protein in *Corynebacterium diphtheriae* is also described in U.S. Pat. No. 5,614,382.

In one embodiment, the host cell is a gram negative host cell. Host cell expression systems like *Escherichia coli, Bacillus* sp., *Pseudomonas* sp., have been extensively discussed in the production of proteins. In one embodiment the polynucleotide of the invention is preferably used for the intracellular expression of $CRM_{197}$ in *Escherichia coli* wherein the host strain is selected from BL21 (DE3), BL21 A1, HMS174 (DE3), DHSct, W31 10, B834, origami, Rosetta, NovaBlue (DE3), Lemo21 (DE3), 17, ER2566 and C43 (DE3).

In a preferred embodiment, the present invention provides a polynucleotide sequence (SEQ ID NO. 2) encoding bacterial toxoid which is optionally ligated into a vector, followed by its insertion in a host cell. The insertion into host cell may be performed by any of the methods known in the art. Such an insertion or transformation may be performed by a physical or a chemical method of transformation. Subsequently, the converted colonies arc selected on petri dishes with added antibiotic.

Suitable vectors used in the present invention include but not limited to pET9a, pET3a, pET3b, pET3c, pET5a, pET5b, pET5c, pET9b, pET9c, pET12a, pTWTN1, pTWTN2, pET12b, pET12c, pET17b and in general, all the vectors that have a strong phage T7 promoter (e.g. pRSETA, B and C [Invitrogen]) and pTYB1, pTYB2, pTYB3 and pTYB4.

In another embodiment, *Escherichia coli* cells are used to express the polynucleotide encoding $CRM_{197}$. The inserted Polynucleotide is verified for proper orientation and position by sequencing. The resultant construct is used to transform host cells by any of the known chemical or physical methods. For example electroporating host cells with an electric field in range 6.5 kV.cm-¹ to 25 kV.cm-¹, a preferred chemical method here which is used to transform host. These cells are allowed to grow for 30 minutes to 120 minutes at 25 to 40° C. in a suitable medium as LB or SOC medium and then transferred to selection media petri plates for 10 to 36 hours, 25 to 40° C. where the positive colonies containing the polynucleotides of invention are selected.

The selection of positive colonies can be done with or without markers. Suitable markers which can be used are selected from, but not limited to, antibiotics such as ampicillin, kanamycin and the like.

The polynucleotide encoding the full length $CRM_{197}$ protein is cloned adjacent to T7 lacI promoter that drives the expression of protein in T7 polymerase positive strains of *Escherichia coli*. The expression of polynucleotide is stringently controlled by T7 promoter which is induced ip the presence of IPTG or in auto-induction mediums The parameters for culturing the host are optimized for high level expression of $CRM_{197}$ protein. In one embodiment, the culture media components, culture conditions including growth temperature, concentration of inducers and induction time is optimized. The culture media used may be selected from, hut not limited to, chemically defined media, LB (Luria-Bertani), TB (Terrific Broth), SOB (Super Optimal Broth), SOC (Super Optimal broth with catabolic repressor), YT broth (Yeast Extract and Tryptone). Super broth, rich media, minimal media, mineral media and the like. The ingredients of media includes, but is not limited to, a carbon source such as, e.g., glucose, sucrose, or glycerol, organic nitrogen source, such as peptone, tryptone, amino acids, or a yeast extract, inorganic nitrogen source is used and this may be selected from among, e.g., ammonium salts, aqueous ammonia, and gaseous ammonia, supplements as supplemented with, e.g., low levels of amino acids, vitamins, peptones, or other ingredients. The culture media may be prepared using the methods known in the art.

The transformed host cells may be tested for expression on small volume such as 5-50 ml in LB, terrific broth or chemically defined medium. The expression may be subjected to different concentrations of inducers ranging from about 0.01 mM, about 0.05 mM, about 0.2 mM, about 0.3 mM, about 0.4 mM, about 0.5 mM, about 0.6 mM, about 0.7 mM, about 0.8 mM, about 0.9 mM and about 1 mM. The polypeptide expression is determined in an electrophoretic set up, preferably in SDS PAGE electrophoresis and viewed as over-expressed bands stained with Coomassie Brilliant Blue (-).

Subsequently, the host cells are inoculated in 500 mL flasks cultures; and allowed to grow under optimal conditions, during which CRMA expression continued from 16 hours to 32 hours. After culturing in constant agitation and preferably under aerobic conditions, the cells are harvested, and lysed. Any of known methods may be applied to lyse cells, preferred method includes a lysis buffer containing a detergent at an appropriate concentration. After lysis, the protein component is pooled in one or more centrifugation steps. Lysis is carried out in a buffer containing Tris-HCl 20-50 mM pH 7.5-8.3, NaCl 100-150 mM, detergent 0.5-1.5% and protease inhibitor 0.5-1.5%, with agitation.

In one embodiment induction temperatures for expression is carried out between 10 to 40° C. In one embodiment $CRM_{197}$ is derived at an induction temperature in a tunable manner, wherein when induction temperature is maintained between 10 to 20° C., more than 80% expressed $CRM_{197}$ is present in soluble fraction,. In another embodiment when the induction temperature is maintained between 25 to 40° C., more than 80% of expressed $CRM_{197}$ obtained is in the insoluble fraction as cytoplasmic inclusion bodies, from which it is purified after a solubilisation step from the pooled cytoplasmic fraction.

In one embodiment cytoplasmic inclusion bodies are solubilized with various concentration of Urea, per se 1M Urea, or 2M Urea, or 3 M Urea, or 4 M Urea, or 5 M Urea, or 6 M Urea, or 7 M Urea, or 8 M Urea, or 9 M Urea.

In the specific embodiment, the yield of soluble $CRM_{197}$ is about 0.1 g/l, 0.25 g/L, 0.5 g/L, about 1 g/L, about 1.5 g/L, about 2 g/L, about 2.5 g/L, about 3 g/L, about 3.5 g L, about 4 g/L, about 4.5 g/L, about 4.5 g/L, about 5 g/L.

In the specific embodiment, the yield of insoluble $CRM_{197}$ is about 0.25 g/L, 0.5 g/L, about 1 g/L, about 1.5 g/L, about 2 g/L, about 2.5 g/L, about 3 g/L, about 3.5 g/L, about 4 g/L, about 4.5 g/L, about 4.5 g/L, about 5 g/L.

The expressed protein is purified using ion exchange chromatographic column followed by affinity chromatography.

Figure 8:
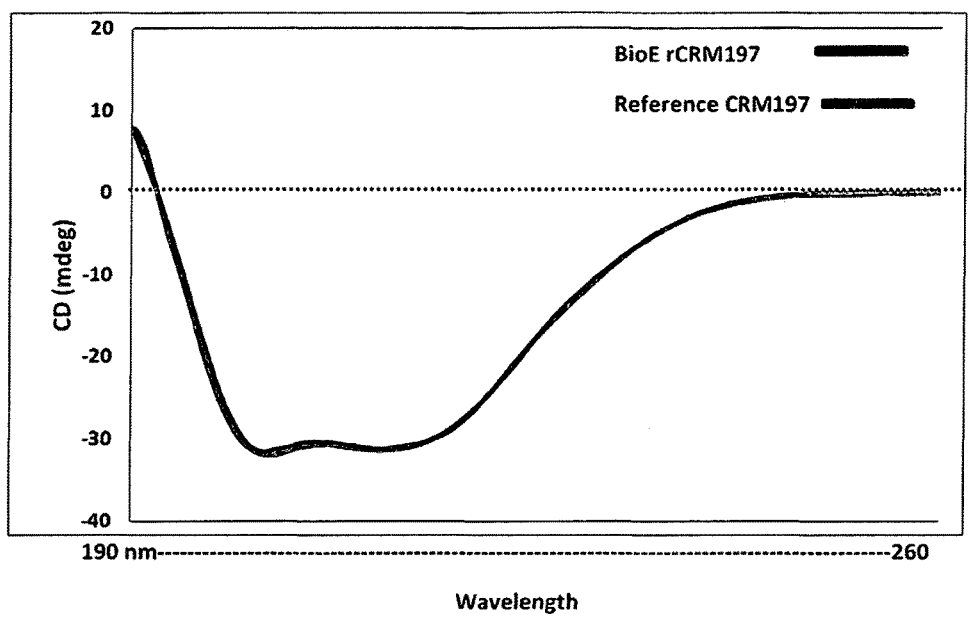
FIG. 8: CD spectra of the recombinant CRM (BioE rCRM) of the present invention was overlapped with the reference $CRM_{197}$. The secondary structure parameter were also analyzed and showed the similarity with reference. The result shows that recombinant CRM (BioE rCRM) of the present invention is structurally similar to the reference
Figure 9:
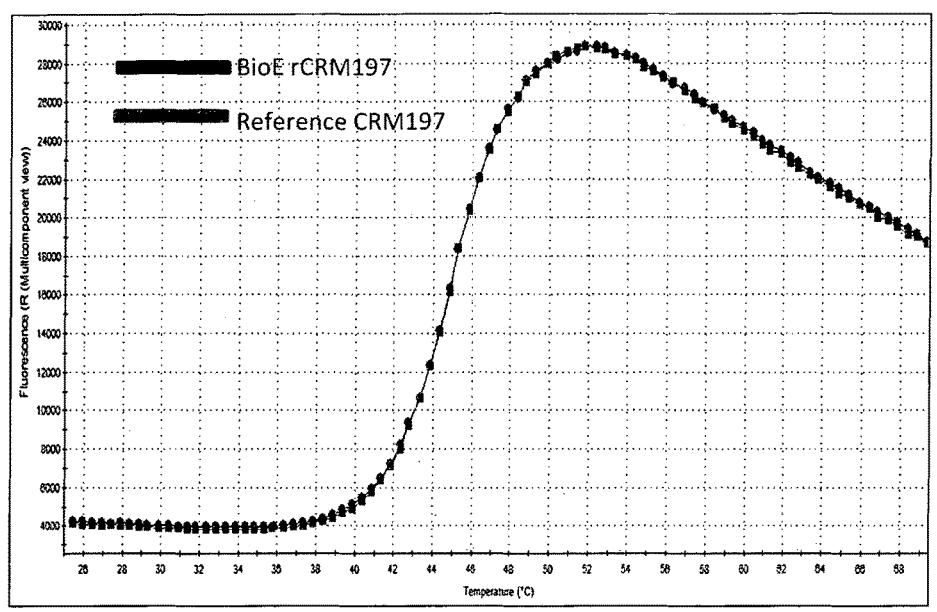
FIG. 9: Confirmation of structural equivalence of recombinant CRM (BioE rCRM) of the present invention with reference using fluorescence assay. Overlay DSF profile of recombinant CRM (BioE rCRM) of the present invention with reference $CRM_{197}$ (C7 CRM). The data confirms the similarity of recombinant CRM (BioE rCRM) of the present invention with the reference C7-$CRM_{197}$.

The invention thus involves more than one subsequent purification steps, and also exploits pI value of $CRM_{197}$ in an ion exchange chromatographic step, whereby it is separated from other contaminating proteins. Finally, the quantity of $CRM_{197}$ is quantified by BCA/Bradford/Lowry Assay and visualized in 10-12% acrylamide gel (SDS-PAGE). The identification of polypeptide is done by Western blot and similar immunoassays. The purity and integrity of purified polypeptide is measured by SDS-PAGE and HPLC methods. The yield of the protein thus expressed is 500-1000 mg/L of the culture medium and can be subsequently varied by modulating the culture additives and conditions, as well as purification steps. The method of the invention also provides an industrially applicable method of tuning the induction time and subsequently modulating the pH and temperature of the chromatographic steps provides simple, inexpensive, and is not laborious. It excludes need of extensive steps involving preparation of buffers or kit or working solution thereof. During the removal of tag there is no need to provide additional buffers or salts or enzymes or equipment. In particular embodiment, the purified $CRM_{197}$ polypeptide readily lacked the first Methionine amino acid, whose presence is not desired in the final $CRM_{197}$ protein and removal of which entails requirement For additional purification steps. The Polypeptide thus obtained is in active and native form; it readily lacks the undesired Methionine as first amino acid without the need of additional steps. $CRM_{197}$ amino acid sequence was analyzed by Insilico/bioinformatics tools; showed about 38.4% hydrophobicity in the protein. The isoelectric point of $CRM_{197}$ is found about 5.81. $CRM_{197}$ protein contained 4 cysteine amino acid residue and 21 proline residues. The refolding of polypeptide is confirmed by functional assays by measuring endonuclease activity over DNA. Biophysical/secondary structure confirmation is done by Circular Dichroism (CD) analysis (FIG. 8) and Differential Scanning Fluorimetry (DSF) (FIG. 9) of polypeptide and compared with commercially available polypeptides (Sigma Aldrich).

Figure 6:
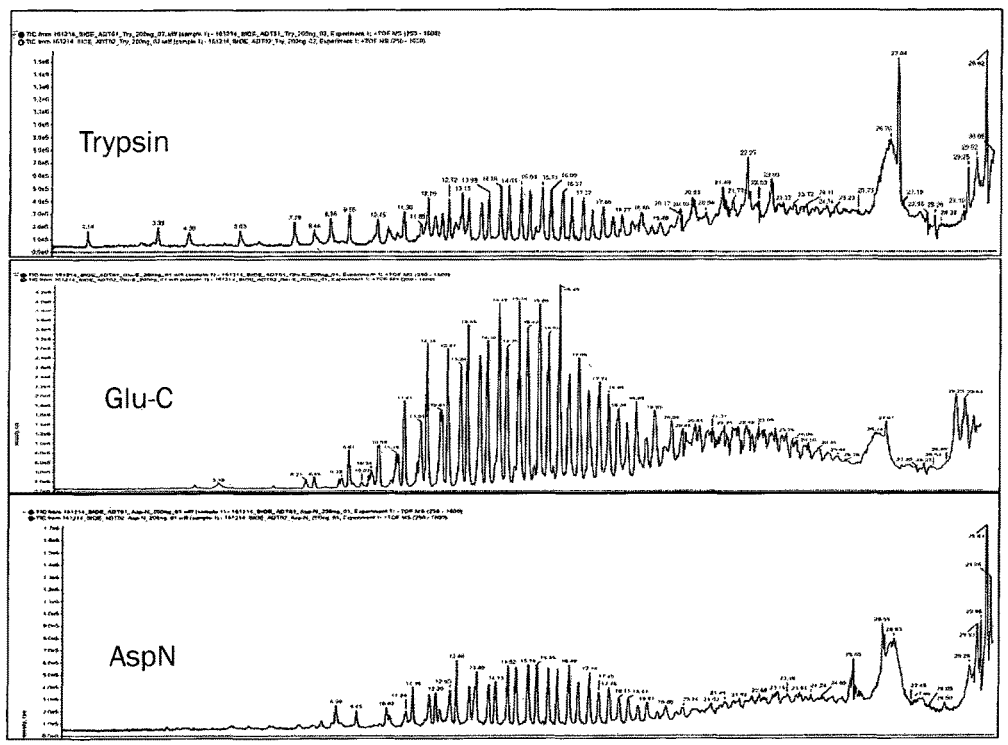
FIG. 6: Peptide mass fingerprint (mass spectrometry) of polypeptide $CRM_{197}$ to define primary amino acid sequence identity. Recombinant CRM (BioE rCRM) of the present invention had 100% sequence similarity with the reference $CRM_{197}$ sequence.
Figure 7:
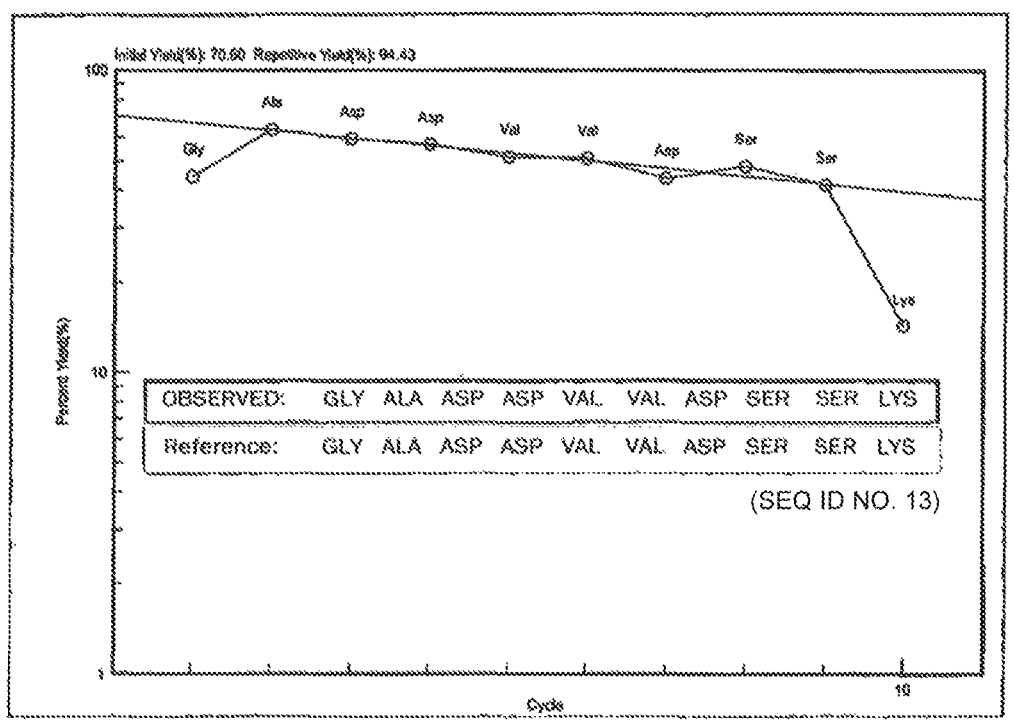
FIG. 7: N-Terminal sequence confirmation of $rCRM_{197}$ by Edman degradation. The 10 amino acid sequence GADDV-VDSSK (SEQ ID NO. 13) (N-Term acetyl) shows starting portion of purified polypeptide. The first amino acid is identified as G.
Figure 10:
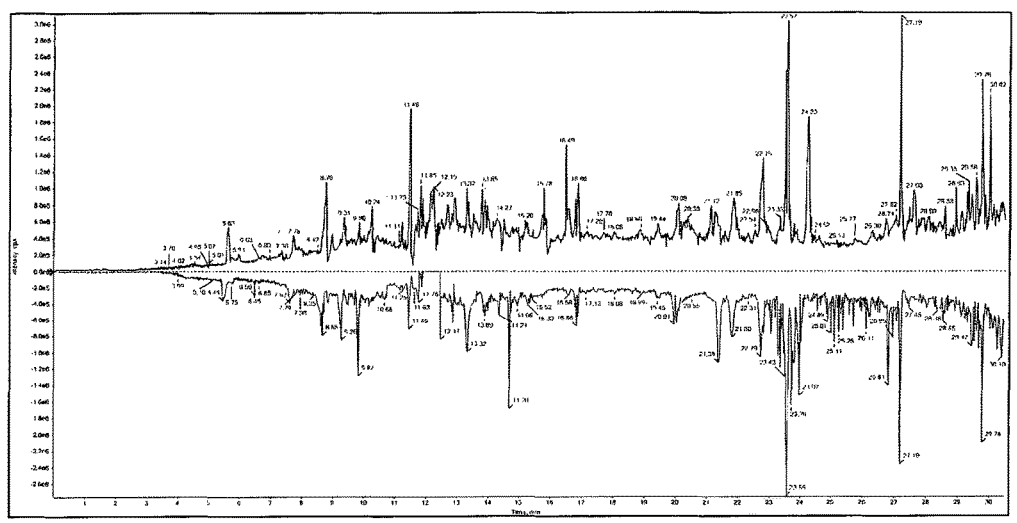
FIG. 10: Confirmation of disulphide bonds. The recombinant CRM (BioE rCRM) of the present invention was analyzed for the presence of correct disulphide bonds in the protein. It is confirmed that two disulphide bonds present in the protein first links amino acid 186 to 201 and second bond links amino acid 461 to 471. The mass spectrometry method was used to analyze the disulphide linkages in $CRM_{197}$.
Figure 11:
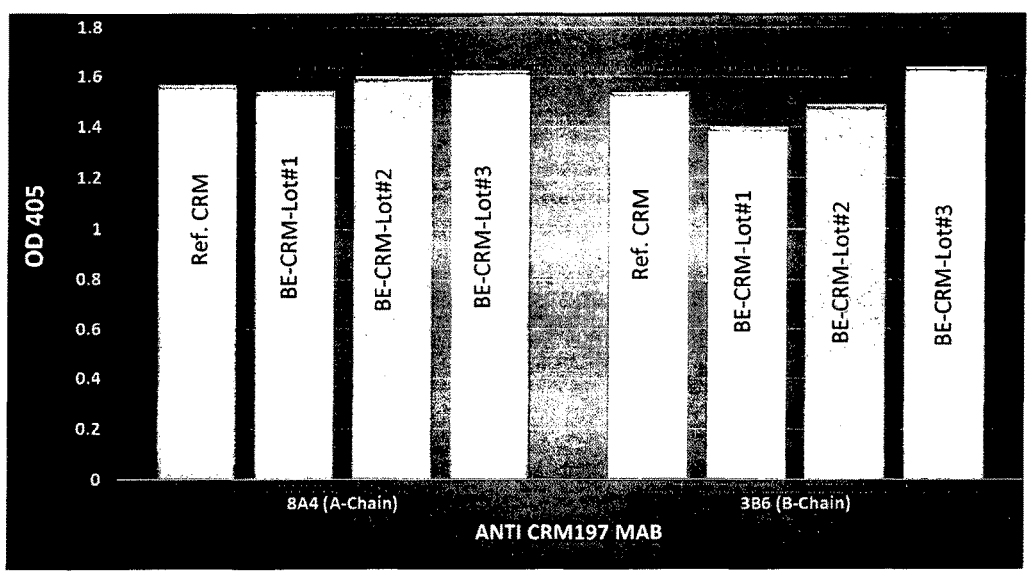
FIG. 11: Confirmation of antigenic similarity of recombinant CRM (BioE rCRM) of the present invention with reference $CRM_{197}$ by $CRM_{197}$ specific ELISA. All the CRMs coming from difference source showed similar recognition profile with monoclonal antibodies.

In another embodiment the presence of correct disulphide linkage was confirmed and compared with commercially available $CRM_{197}$ polypeptides (Sigma Aldrich) (FIG. 10). Also the correctness of amino acid sequence of produced polypeptide was confirmed by digesting the $CRM_{197}$ polypeptide with multiple proteases and mapping of amino acid sequence (FIG. 6). The N-terminal amino acid sequence of produced polypeptide is confirmed by Edman degradation sequencing (FIG. 7).

In a preferred embodiment, the present invention provides an optimized polynucleotide sequence (SEQ ID NO. 2) and its structural variants having equal to or more than 70% similarity, preferably 85 to 99% similarity, useful for high level expression of polypeptide for $CRM_{197}$.

In yet another preferred embodiment, the present invention provides an optimized polynucleotide sequence (SEQ ID NO. 2) useful for high level expression of polypeptide for $CRM_{197}$ in *Escherichia coli* cell.

In another preferred embodiment, the present invention provides high level expression of Diphtheria toxin or $CRM_{197}$ or variants thereof, using nucleic acid SEQ ID NO: 2 or a variant thereof in gram negative bacterial cell, preferably *Escherichia coli* comprising the steps of;
a) selecting the gene SEQ ID NO: 2 or its variant thereof, which encodes polypeptide $CRM_{197}$,
b) sub cloning the gene SEQ ID NO: 2, into an expression vector,
c) transforming the host *Escherichia coli* cell with the expression vector of step b;
d) culturing the transformed host cell in a culture media suitable for the expression of the toxin protein;
e) inducing the expression of fusion protein by adding IPTG as inducing agent at temperature in the range of 30 to 40° C.,
f) extracting the bacterial toxin in insoluble form from the host cell and
g) purifying the $CRM_{197}$ in pure form with yield more than 0.5 mg/l.

The purification is carried out using chromatography. The chromatography technique may be affinity chromatography, gel filtration, high pressure liquid chromatography (HPLC) or ion exchange chromatography or combination of two or more. Preferably, when $CRM_{197}$ is associated with tag fusion protein, affinity chromatography may be used to separate $CRM_{197}$ from other proteins.

In another preferred embodiment, a simple step involving a shift in temperature and pH of the column conditions also facilitate the elution of $CRM_{197}$ from the associated tag. More particularly, a pH in the range of 6.5-8.5 and temperature in the range of 4° C.-30° C. may be used to separate $CRM_{197}$ from tag.

In other embodiments, the $CRM_{197}$ prepared according to the present invention is used to conjugate with polysaccharide molecules isolated from *Salmonella typhi*, *Salmonella paratyphi*, *Pneumococcus*, *Haemophilus influenzae*, *Meningococcus*, *Streptococcus pneumoniae* and other pathogenetic bacteria.

In another embodiment, the $CRM_{197}$ prepared according to the present invention is used as a conjugated carrier for vaccines such as those against *Salmonella typhi*, *Salmonella paratyphi*, *Pneomococcus*, *Haemophilus influenzae*, *Meningococcus*, *Streptococcus pneumoniae* and other pathogenetic bacteria.

The present invention will be more specifically illustrated with reference to the following examples. However, it should be understood that the present invention is not limited by these examples in any manner but includes variations thereof within the parameters described herein, as can be known to those well-versed in the art.

Example 1

Step (i): Synthesis of Novel $CRM_{197}$ Gene

Full length $CRM_{197}$ gene was optimized according to *Escherichia coli* codon usage. The following parameters were used for $CRM_{197}$ gene optimization: Codon Usage Bias, GC content, mRNA Secondary Structure, Custom Desired Patterns, Custom Undesired Patterns, Repeat Sequences (direct repeat, inverted repeat, and dyad repeat). Restriction Enzyme Recognition Sites (deletion or insertion).

Optimized $CRM_{197}$ gene (SEQ ID NO. 2) was cloned at multiple cloning site of pUC57 plasmid vector using BamHI and Sapi restriction sites, generating pUC57_CRMw. The vectors containing $CRM_{197}$ gene was transformed in *Escherichia coli* DH5a host and clones was selected on LB+Kanamycin plate. The presence and correctness of $CRM_{197}$ gene in pUC57 was confirmed by restriction digestion of pUC57_$CRM_{197}$ plasmid by Age I (located in $CRM_{197}$ gene) and Nde I (located in pUC57 plasmid). Further the sequence of $CRM_{197}$ was confirmed by PCR and DNA sequencing.

Step (ii): Insertion of $CRM_{197}$ into Expression Vector pTWI I

*Escherichia coli* DH5a carrying pUC57_$CRM_{197}$ was grown over night in LB-Kanamycin in 50 ml volume. Bacteria were centrifuged and pellet was used for plasmid isolation, isolation of plasmid was done by using Qiagen plasmid mini-prep kit using manufacturer instructions. Isolated plasmid was quantified by nano-drop.

$CRM_{197}$ (SEQ ID NO. 2) from pUC57 was excised, Sag plasmid was digested with restriction endonucleases BamHI and SapI. The digested plasmid was run on 1% agarose gel and band corresponding to $CRM_{197}$ gene (SEQ ID NO. 2, ~1.6 kb) was purified by using Qiagen Gel extraction kit using manufacturer's instructions. Subsequently the 5 µg of expression plasmid pTWIN1 was also digested with BamHI and SapI to generate restriction sites in it that is compatible with $CRM_{197}$ gene. The digested pTWIN1 was also purified from gel using Qiagen Gel extraction kit with manufacturer's instructions.

The digested $CRM_{197}$ gene was ligated in pTWIN1 using T4 ligase based DNA ligation kit (Promega) using manufacturer's instructions. Vector (pTWIN1) and Insert ($CRM_{197}$) was mixed in 1:3, 1:4, 1:5 ratio in the presence of T4 DNA ligase and buffers in a 20 µl reaction volume. Ligation mixture was incubated overnight at 16° C. Next morning 5 µl of ligation mixture was added/transformed in BL21-DE3 *Escherichia coli* expression host. BL21 was transformed by using chemical transformation protocol. The ligation+ BL21 cells were incubated in ice for 30 min. After incubation heat shock was given for 45 seconds at 42° C. Sample was cooled at room temperature and 500 µl SOC medium was added into it. The tube with transformants was incubated for 2 hours at 37° C. with 200 rpm. From which 100 µl mixture was plated on LB+Ampicillin plate for screening of transformants.

$CRM_{197}$ expression BL21-DE3 iransformants were selected next morning from Luria Broth+Ampicillin plates. Of these 5 clones growing on Luria Broth+Ampicillin were selected and grown in 10 ml Luria Broth+Ampicillin media for overnight at 37 degrees, 200 rpm. Culture was centrifuged and plasmid was extracted from cell pellet using Qiagen plasmid extraction kit.

To verify the correctness of clone, 2 µg plasmid was digested with Agel and Apal restriction endonuclease, respectively. Agel site is present in $CRM_{197}$ and Apal is in pTWIN 1. Therefore double digestion with both the enzymes used for confirmation of correct clone. The clone was designated as pTWIN1_CRMw (BL21-DE3). Furthermore clones were confirmed by. PGR using $CRM_{197}$ gene specific primers and DNA sequencing. The glycerol stock of BL21 expressing CRMm was made by growing bacteria in 10 ml Luria Broth+Ampicillin overnight. Next morning 40% sterilized Glycerol was added into culture and 1 ml aliquot was dispensed into cryovial. Vials were stored at -80 degree for further use in expression analysis.

Step (iii): Confirmation of Expression of CRMw:

BL21 clone stored at −80 degrees was streaked on Luria Broth+Ampicillin plate. Plate was incubated overnight at 37 degrees. Single colony was picked up and inoculated in 50 ml Luria Broth+Ampicillin media in 150 ml flask. Flask was incubated at 37 degrees, 200 RPM until OD600=1. Once OD reaches to desired point, 5 ml culture was drawn which is used as uninduced culture. Uninduced culture was kept on ice until use. To induce the expression of $CRM_{197}$ gene 0.5 mM IPTG was added to remaining 45 ml culture and flask was further incubated for additional 4 hours at 30 degree and 200 rpm rotation. Induced culture was harvested after 4 hours and expression of $CRM_{197}$ was examined by SDS-PAGE (FIG. 1) and Western Blot (FIG. 2).

For SDS-PAGE analysis 1 ml culture of induced and uninduced culture (both normalized for OD600=1) was taken into 1.5 ml Eppendorf tube. The tube was centrifuged and pellet was resuspended into 50 μl PBS. In this suspension 50 μl SDS-PAGE loading buffer with reducing agent (2×) was added. The mixture was boiled at 100 degree for 5 min. Sample was cooled at room temperature and 20 μl of uninduced and induced culture was loaded in the 4-12% Tris Glycine gel. The gel was run for 1.5 hours at 150 volts. Gels were taken out and incubated in Coomassie Brilliant Blue dye for 1 hour After staining gel was detained in destaining solution containing 40% methanol=10% acetic acid for 3 hours. The $CRM_{197}$ expression was visualized as ~58 KD protein that is only visible in induced culture. For western blot a separate set of gel was run in the same manner as SDS-PAGE and gel was blotted on PVDF (polyvinylidene difluoride membrane). The membrane was immunoblotted by anti- $CRM_{197}$ antibody. In the western blot CRMw appeared as single immunoreactive band at ~58 Kd. No $CRM_{197}$ specific band was observed in uninduced culture. This experiment confirms that the done generated in the present study can express r$CRM_{197}$ protein. These clones were further used for large scale production and purification of $CRM_{197}$.

Step (iv): Fermentation and Purification of $CRM_{197}$ from BL21 *Escherichia coli*

One ml vial of BL21 *Escherichia coli* cells was inoculated into 50 ml LB+Amp media and grown overnight at 37 degrees, 200 rpm. Fermentation was done at 20 L scale. *Escherichia coli* cells were inoculated to the fermenter and cultivated at 30 degrees centigrade. The culture was induced with 0.5 mM IPTG at OD600=20. After 12 hours post induction fermentation culture was harvested and cell pellet was prepared by centrifugation. Cell pellet was lysed mechanically in homogenizer. Inclusion body (which contains the desired protein $CRM_{197}$) was isolated by centrifugation of cell lysates. Supernatant was discarded and pellet was retained which contains Inclusion body (IBs). IBs were homogenized by resuspending pellet in 8M urea and protein was purified by ion exchange chromatography. Quantification of $CRM_{197}$ at fermentation level was measured. Whole cells lysates was run on SDS-PAGE along with the known amount of BSA as standard. The quantification of $CRM_{197}$ which appeared as ~58 KD band in SDS-PAGE (FIG. 3) was quantified by densitometry analysis. BSA was used as reference for quantification. The total amount of protein was found as 1.4 gram $CRM_{197}$/liter of BL21 *Escherichia coli* cells.

Solubilization test of the $CRM_{197}$ prepared above was carried out in Electrophoretic gel run (SDS PAGE 12%) showing test conducted on solubilization of $CRM_{197}$, Lane 1: Urea solubilized fraction of $CRM_{197}$; Lane 2: Supernatant; Lane 3: Sample from first pellet wash; Lane 4: Sample pooled from 2nd pellet wash (FIG. 4).

Figure 5:
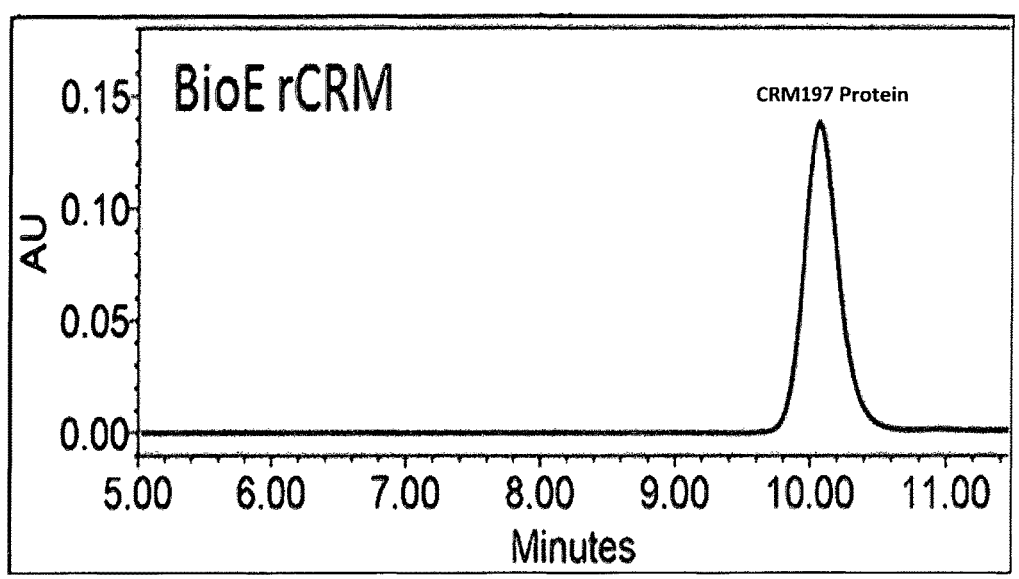
FIG. 5: Size exclusion chromatography (SEC-HPLC) wherein major eluted peak shows the presence of $CRM_{197}$ in the sample.

Presence of CRM$_{197}$ in the sample was determined by Size exclusion chromatography (SEC-HPLC) wherein major eluted peak shows the presence of CRMw in the sample (FIG. 5).

Primary amino acid sequence of the CRM$_{197}$ prepared above was determined by Peptide mass fingerprint (mass spectrometry) and had 100% sequence similarity with the reference CRM$_{197}$ sequence (FIG. 6).

A. Peptic digest of BE rCRM analyzed by LC-MS.

B. Sequence coverage in Trypsin, Glu-C and Asp-N digest $CRM_{197}$ (identical to SEQ ID NO. 1 i.e. shows 100% homology)

N-Terminal sequence of rCRMm prepared above was confirmed by Edman degradation. The 10 amino acid sequence GADDVVDSSK (SEQ ID NO. 13) (N-Term acetyl) shows starting portion of purified polypeptide. The first amino acid is identified as G (FIG. 7).

CD spectra of the $CRM_{197}$ prepared above was overlapped with the reference $CRM_{197}$. The result shows that recombinant $CRM_{197}$ prepared above is structurally similar to the reference $CRM_{197}$ (FIG. 9).

Confirmation of disulphide bonds of $CRM_{197}$ prepared by the above method was analyzed (FIG. 10) and was confirmed by mass spectrometry that two disulphide bonds present in the protein first links amino acid 186 to 201 and second bond links amino acid 461 to 471.

TABLE I

| Cystine Numbering | Peptide sequence |
|---|---|
| 186 | GQDAMYEYMAQACAGNR (SEQ ID NO: 11) |
| 201 | SVGSSLSCINLDWDVIR (SEQ ID NO: 12) |
| 461 | CR |
| 471 | AIDGDVTFCRPK (SEQ ID NO: 14) |

TABLE Ii

| Tryptic peptides chain combination | Theoretical Mono m/z | Observed Mono m/z |
|---|---|---|
| Cys 186-201 | 935.6706 | 935.6694 |
| Cys 461-471 | 913.9558 | 913.9539 |

Antigenic similarity of $CRM_{197}$ prepared by the above method with reference $CRM_{197}$ was confirmed by $CRM_{197}$ specific ELISA. All the CRMs coming from difference source showed similar recognition profile with monoclonal antibodies (FIG. 11).

We claim:

1. A polynucleotide having the sequence set forth as SEQ ID NO. 2 or a variant thereof which is at least 85% homologous to SEQ ID NO. 2.

2. The polynucleotide of claim 1, wherein the variant thereof is at least 88% homologous to SEQ ID NO. 2.

3. A process for the production of polypeptide, comprising steps of:
   a) selecting the polynucleotide of claim 1,
   b) optionally ligating the polynucleotide sequence of step (a) into a suitable vector,
   c) inserting or transforming the polynucleotide sequence into an *Escherichia coli* host cell to generate a transformed host cell,
   d) culturing the transformed host cell in a culture media for high level expression of a $CRM_{197}$ polypeptide from the polynucleotide sequence of step (a),
   e) maintaining an induction temperature between 10 to 40° C. to produce the $CRM_{197}$ polypeptide,
   f) extracting the $CRM_{197}$ polypeptide from the transformed host cell, and
   g) purifying the $CRM_{197}$ polypeptide to obtain pure $CRM_{197}$ polypeptide with high yield.

4. The process of claim 3, wherein the suitable vector is a plasmid vector selected from the group consisting of pET9a, pET3a, pET3b, pET3c, pET5a, pET5b, pET5c, pET9b, pET9c, pET12a, pTWIN1, pTWIN2, pET12b, pET12c, and pET17b.

5. The process of claim 3, wherein the *Escherichia coli* host cell is a strain selected from the group consisting of BL21 (DE3), BL21 A 1, HMS174 (DE3), DH5ot, W31 10, B834, Lemo21 (DE3), T7, ER2566, and C43 (DE3).

6. The process of claim 3, wherein the yield of the $CRM_{197}$ polypeptide is about 0.1 g/L, 0.25 g/L, 0.5 g/L, about 1 g/L, about 1.5 g/L, about 2 g/L, about 2.5 g/L, about 3 g/L, about 3.5 g/L, about 4 g/L, about 4.5 g/L, about 4.5 g/L, or about 5 g/L.

7. The process of claim 3, wherein at least a portion of the $CRM_{197}$ polypeptide is localized to the periplasm by providing a suitable induction temperature without any heterologous sequence for directed transport into the periplasmic space.

8. The process of claim 3, wherein the $CRM_{197}$ polypeptide is a carrier protein.

9. The process of claim 3, wherein the $CRM_{197}$ polypeptide is conjugated with polysaccharide molecules isolated from *Salmonella typhi, Salmonella paratyphi, Pneumococcus, Haemophilus influenzae, Meningococcus, Streptococcus pneumoniae*, or other pathogenetic bacteria.

10. An expression vector comprising the polynucleotide of claim 1 for transforming an *Escherichia coli* host cell.

11. The expression vector of claim 10, wherein the expression vector is a plasmid vector selected from the group consisting of pET9a, pET3a, pET3b, pET3c, pET5a, pET5b, pET5c, pET9b, pET9c, pET12a, pTWIN1, pTWIN2, pET12b, pET12c, and pET17b.

12. A polynucleotide having the sequence selected from the group consisting of SEQ ID NO. 3, 4, 5, 6, 7, 8, 9, and 10.

13. An expression vector comprising the polynucleotide of claim 12 for transforming an *Escherichia coli* host cell.

14. The expression vector of claim 13, wherein the expression vector is a plasmid vector selected from the group consisting of pET9a, pET3a, pET3b, pET3c, pET5a, pET5b, pET5c, pET9b, pET9c, pET12a, pTWIN1, pTWIN2, pET12b, pET12c, and pET1 7b.

* * * * *